(12) United States Patent
Cho et al.

(10) Patent No.: US 10,688,085 B2
(45) Date of Patent: Jun. 23, 2020

(54) USE OF STATIN-BASED DRUG FOR TREATMENT OF EML4-ALK-POSITIVE NON-SMALL CELL LUNG CANCER PROGRESSING ON ALK INHIBITOR

(71) Applicants: University-Industry Foundation, Yonsei University, Seoul (KR); Jeuk Co., Ltd., Gyeongsangbuk-do (KR)

(72) Inventors: Kyoung-Je Cho, Gyeongsangbuk-do (KR); Byoung Chul Cho, Seoul (KR); Mi-Ran Yun, Gyeonggi-do (KR); Kyoung-Ho Pyo, Seoul (KR); Han Na Kang, Seoul (KR); Hun-Mi Choi, Seoul (KR)

(73) Assignees: UNIVERSITY-INDUSTRY FOUNDATION, YONSEI UNIVERSITY, Seoul (KR); JEUK CO., LTD., Gyeongsangbuk-do (KR)

( * ) Notice: Subject to any disclaimer, the term of this patent is extended or adjusted under 35 U.S.C. 154(b) by 0 days.

(21) Appl. No.: 16/070,146

(22) PCT Filed: Jan. 13, 2017

(86) PCT No.: PCT/KR2017/000502
§ 371 (c)(1),
(2) Date: Jul. 13, 2018

(87) PCT Pub. No.: WO2017/123063
PCT Pub. Date: Jul. 20, 2017

(65) Prior Publication Data
US 2019/0046514 A1    Feb. 14, 2019

(30) Foreign Application Priority Data

Jan. 14, 2016 (KR) .................. 10-2016-0004510

(51) Int. Cl.
*A61K 31/40* (2006.01)
*A61K 31/4418* (2006.01)
*A61K 31/366* (2006.01)
*A61K 31/505* (2006.01)
*A61K 31/404* (2006.01)
*A61K 35/00* (2006.01)
*G01N 33/574* (2006.01)
*G01N 33/543* (2006.01)
*A61P 35/00* (2006.01)

(52) U.S. Cl.
CPC ........ *A61K 31/4418* (2013.01); *A61K 31/366* (2013.01); *A61K 31/40* (2013.01); *A61K 31/404* (2013.01); *A61K 31/505* (2013.01); *A61P 35/00* (2018.01); *G01N 33/543* (2013.01); *G01N 33/574* (2013.01); *G01N 33/57423* (2013.01); *G01N 2333/912* (2013.01)

(58) Field of Classification Search
CPC .... A61K 31/366; A61K 31/40; A61K 31/404; A61K 31/4418; A61K 31/505; G01N 33/543; G01N 33/574; G01N 33/57423; G01N 2333/912; A61P 35/00
See application file for complete search history.

(56) References Cited

U.S. PATENT DOCUMENTS

2011/0118298 A1\* 5/2011 Fritz ................ G01N 33/57492
                                                              514/291
2018/0021306 A1\* 1/2018 Pan ..................... A61K 39/395
                                                              514/410

FOREIGN PATENT DOCUMENTS

WO    2011115725 A2    9/2011

OTHER PUBLICATIONS

Chen et al., "Atorvastatin Overcomes Gefitinib Resistance in KRAS Mutant Human Non-Small Cell Lung Carcinoma Cells", Cell Death and Disease, vol. 4, paper No. e814, pp. 1-13, 2013.
Sasaki et al., "The Biology and treatment of EML4-ALK Non-Small Cell Lung Cancer", European Journal of Cancer, vol. 46, pp. 1773-1780, 2010.
Warita et al., "Statin-induced Mevalonate Pathway Inhibitiion Attenuates the Growth of Mesenchymal-like Cancer cells that Lack Functional E-Cadherin Medicated Cell Cohesion", Scientific Reports, vol. 4, paper No. 7593, pp. 1-8, 2014.
Tan et al., "Statins and the Risk of Lung Cancer: A Meta-Analysis", Plos One, vol. 8, No. 2, paper No. e57349, pp. 1-9, 2013.
Int'l Search Report dated Mar. 13, 2017 in Int'l Application No. PCT/KR2017/000502.

\* cited by examiner

*Primary Examiner* — Sarah Pihonak
(74) *Attorney, Agent, or Firm* — Panitch Schwarze Belisario & Nadel LLP

(57) ABSTRACT

Provided are a pharmaceutical composition exhibiting therapeutic efficacy against EML4-ALK-positive non-small cell lung cancer that has acquired resistance to an ALK inhibitor and a method for treating the non-small cell lung cancer. Further, provided is information for drug selection for determining whether to administer a statin-based drug to a patient group with EML4-ALK-positive non-small cell lung cancer.

6 Claims, 22 Drawing Sheets

[FIG 1a]
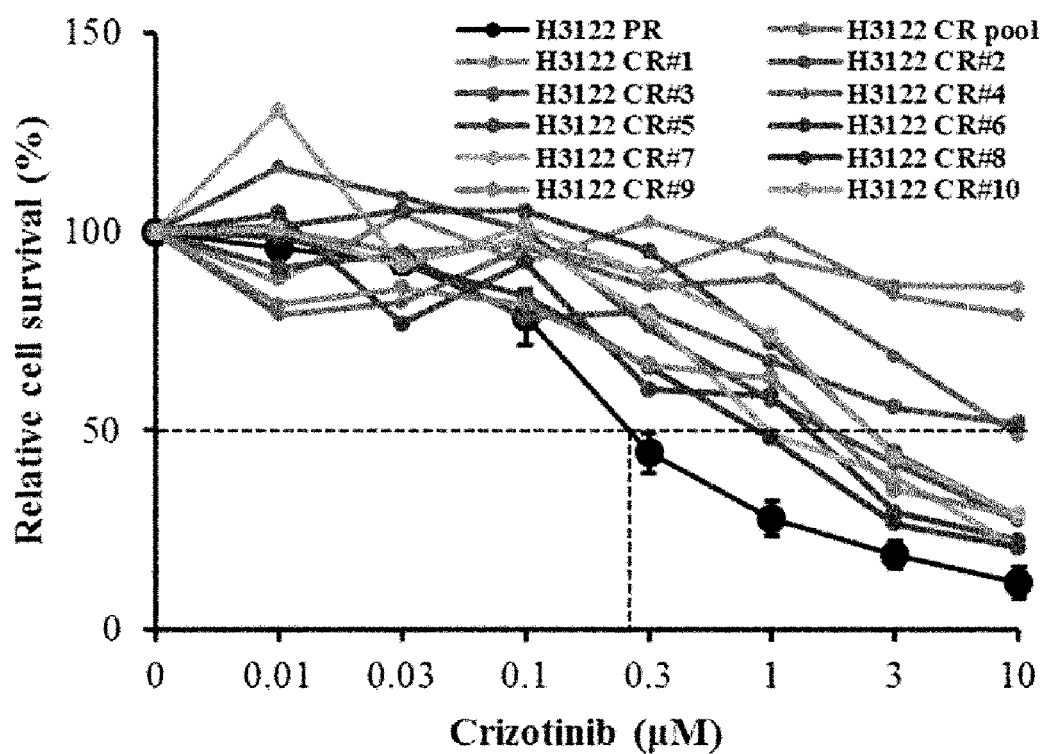

[FIG 1b]
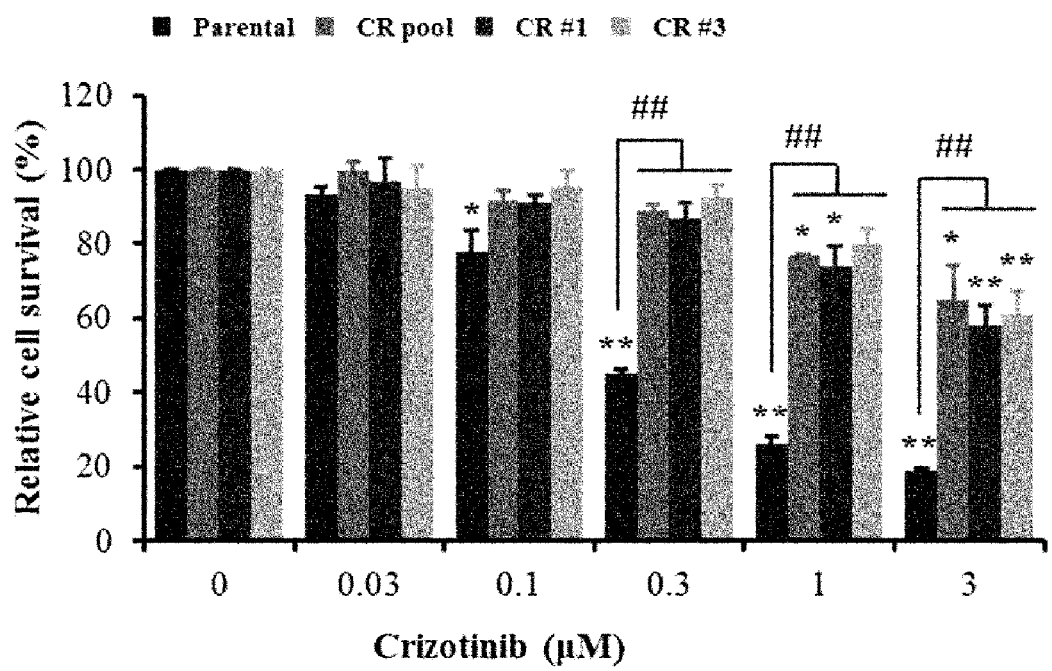
[FIG 1c]
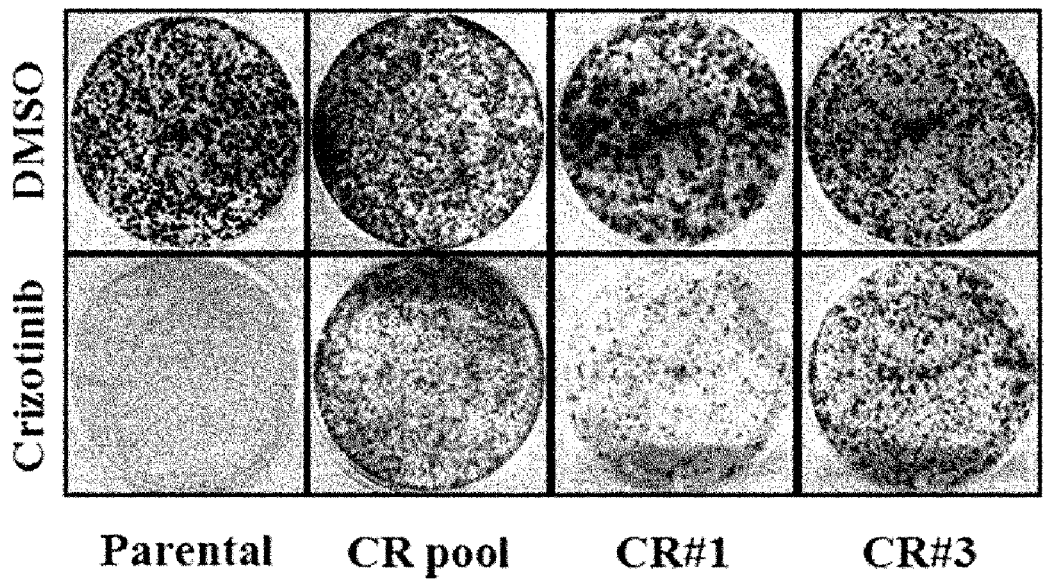

[FIG 2]
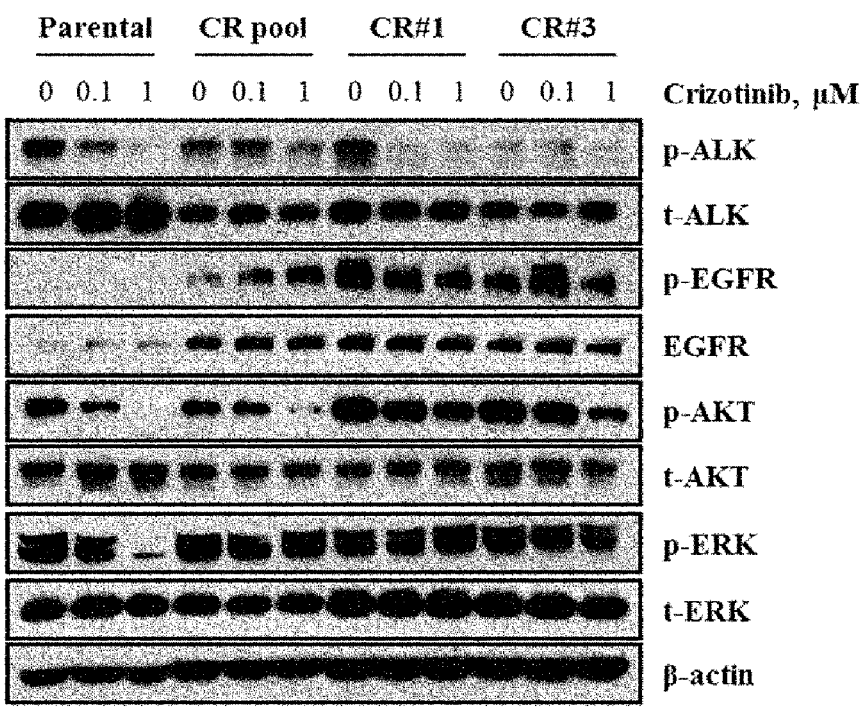

[FIG 3a]
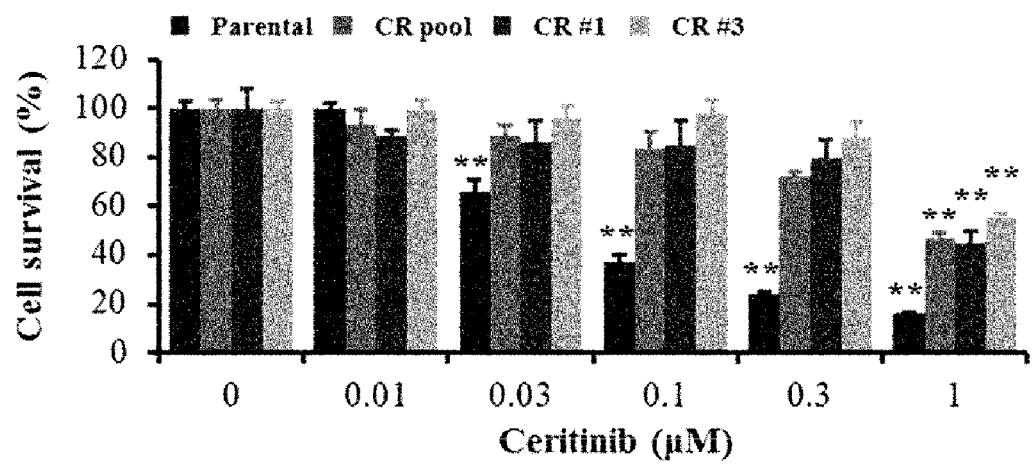
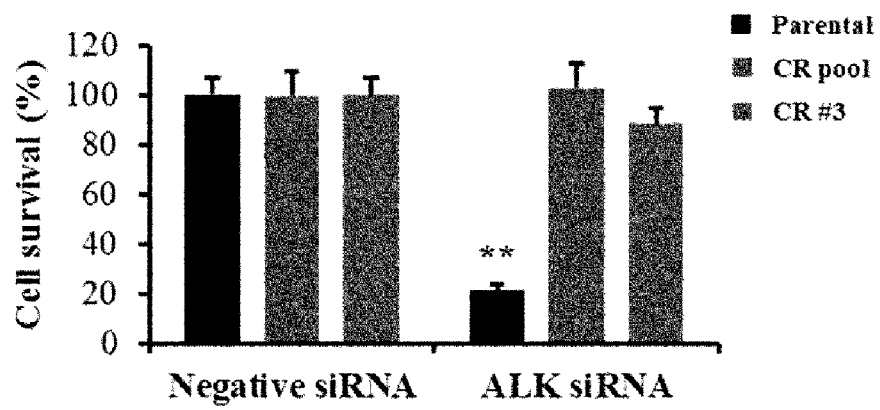

[FIG 3b]
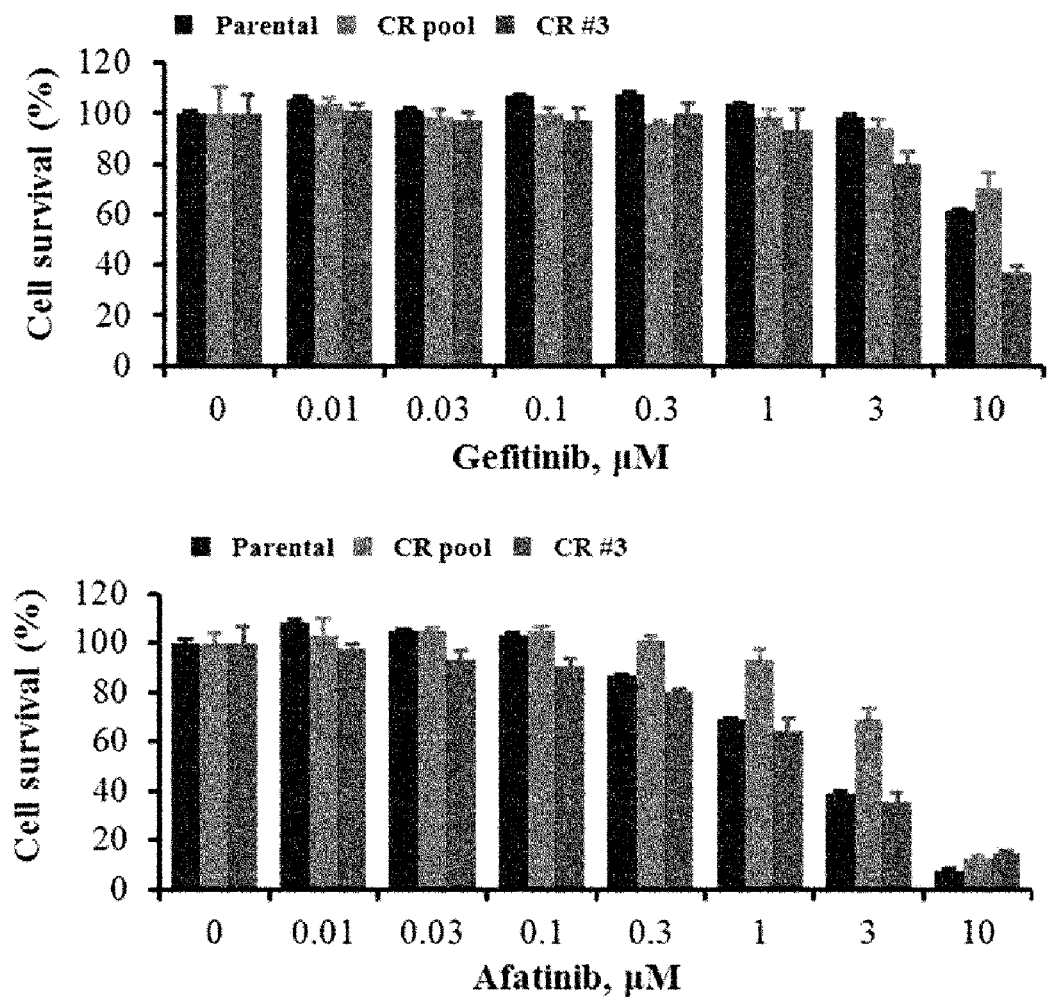

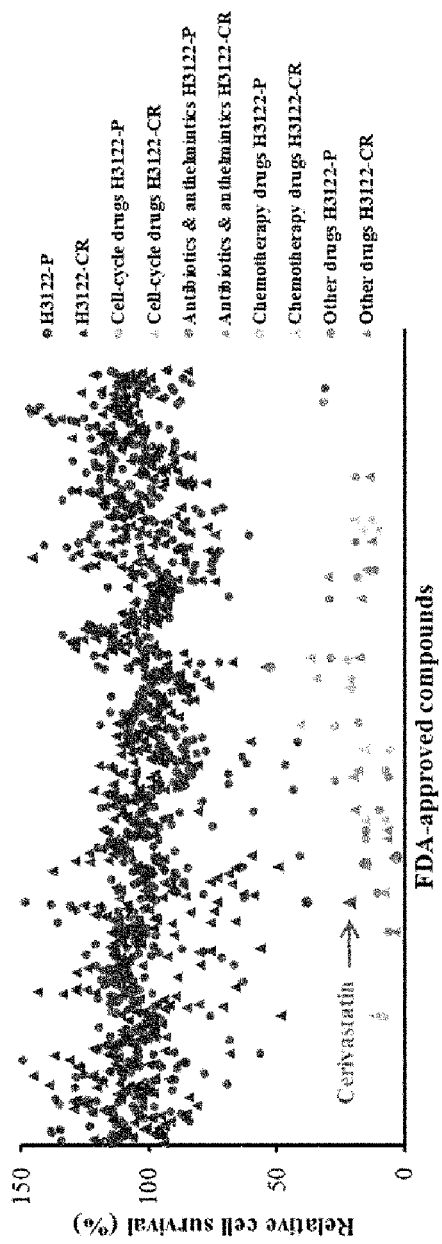
[FIG 4a]

[FIG 4b]
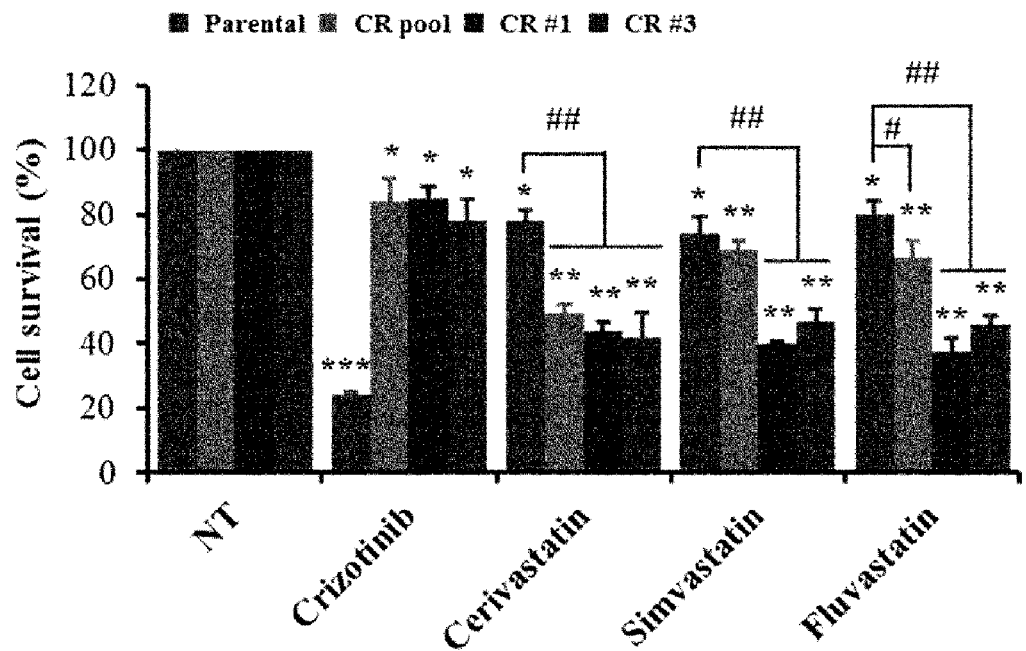
[FIG 4c]
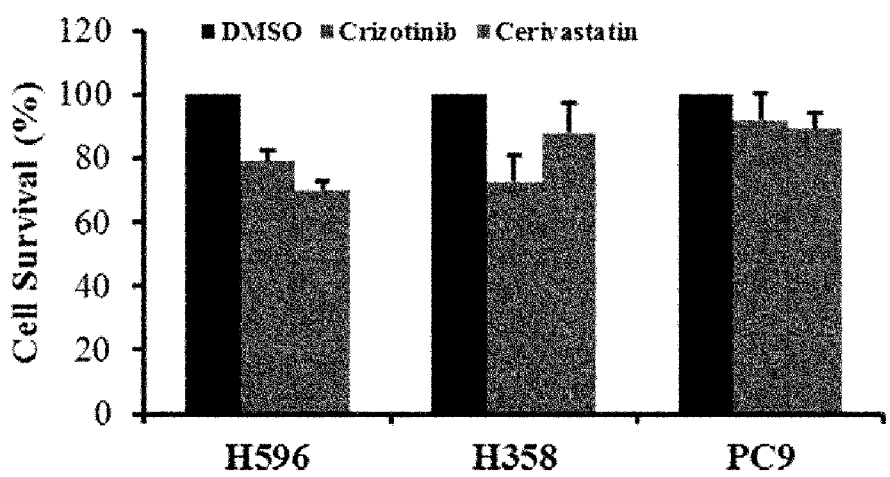

[FIG 5a]
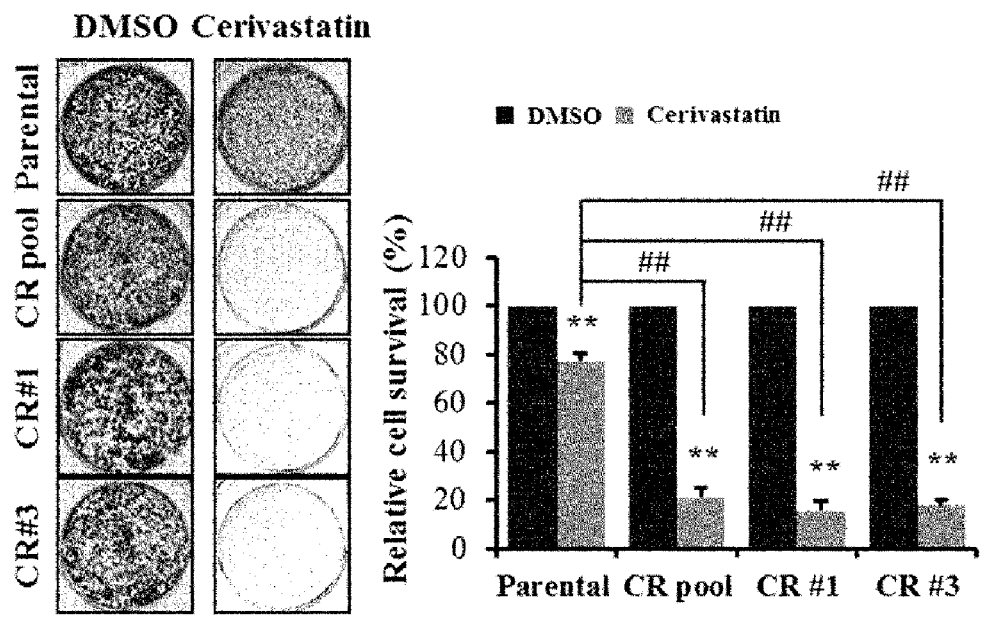
[FIG 5b]
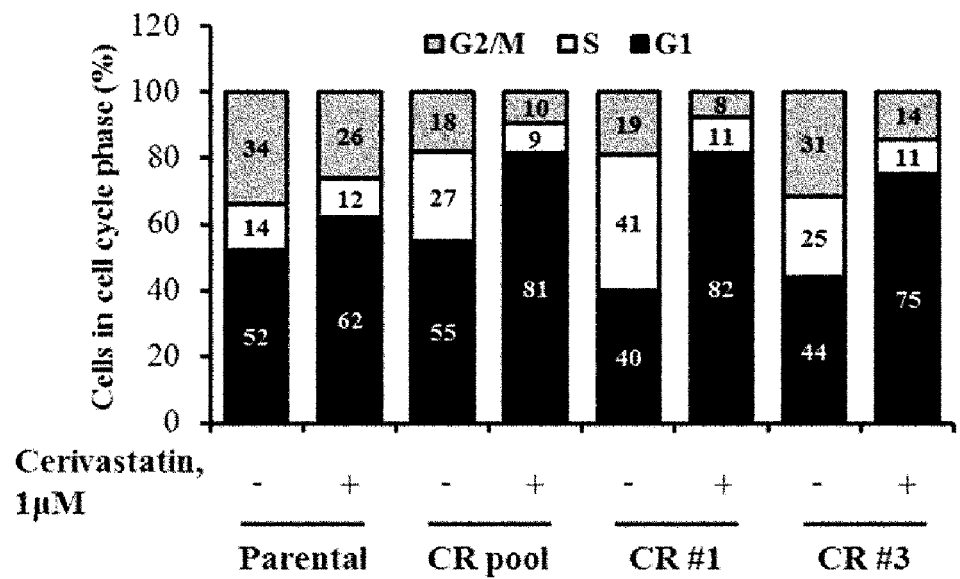

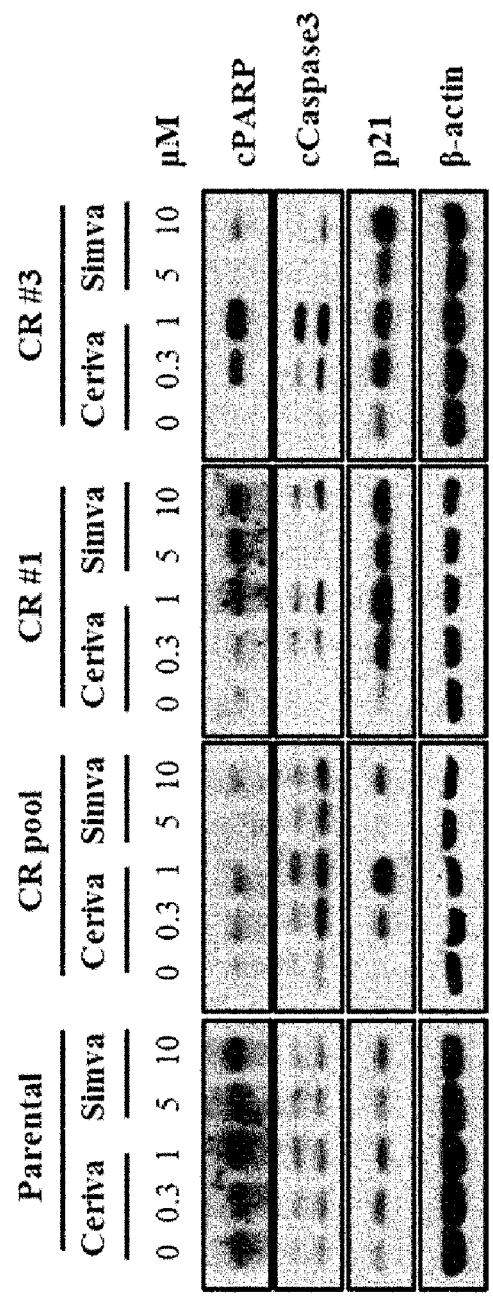
[FIG 5c]

[FIG 6a]
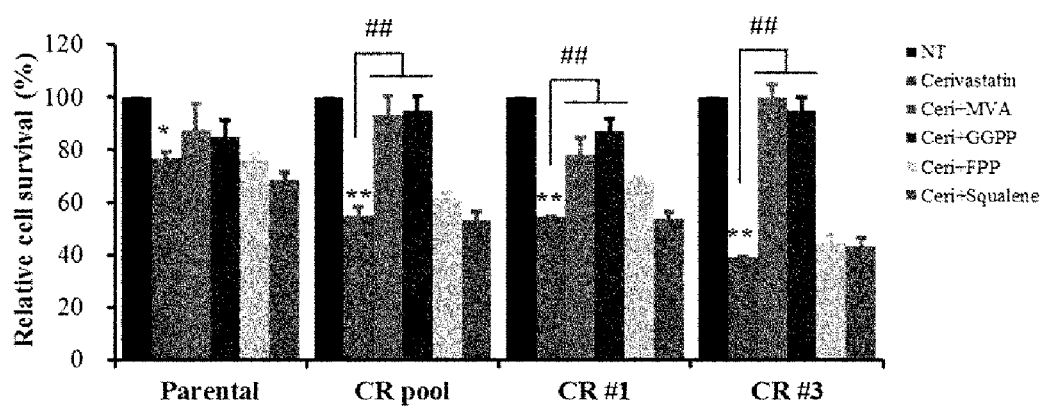
[FIG 6b]
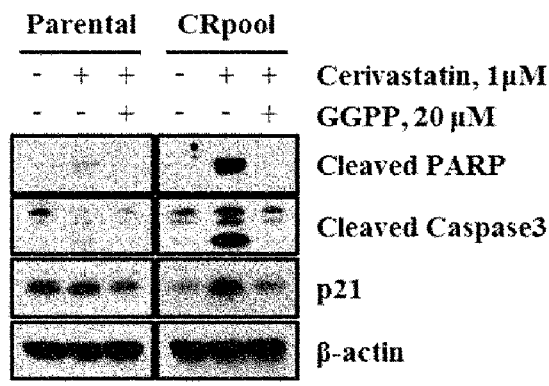

[FIG 6c]
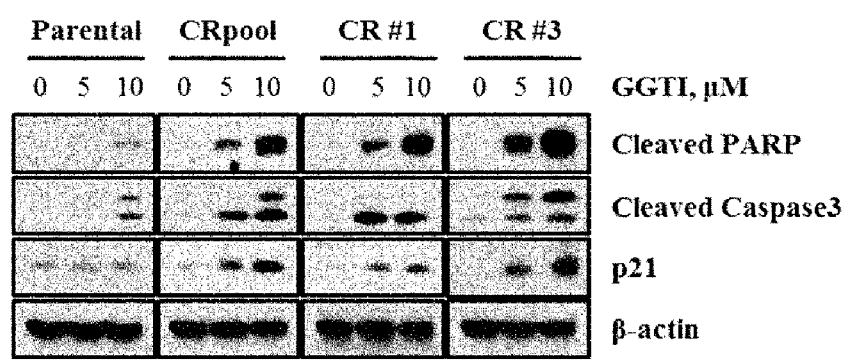

[FIG 7a]
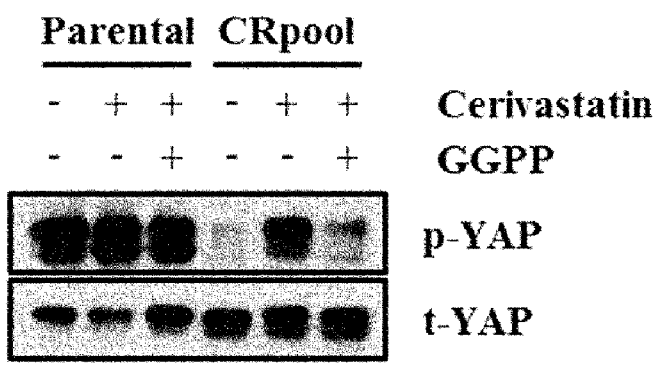
[FIG 7b]
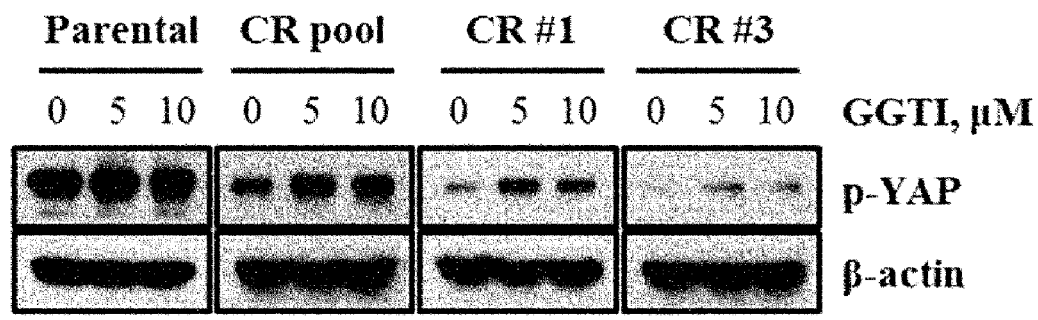

[FIG 7c]
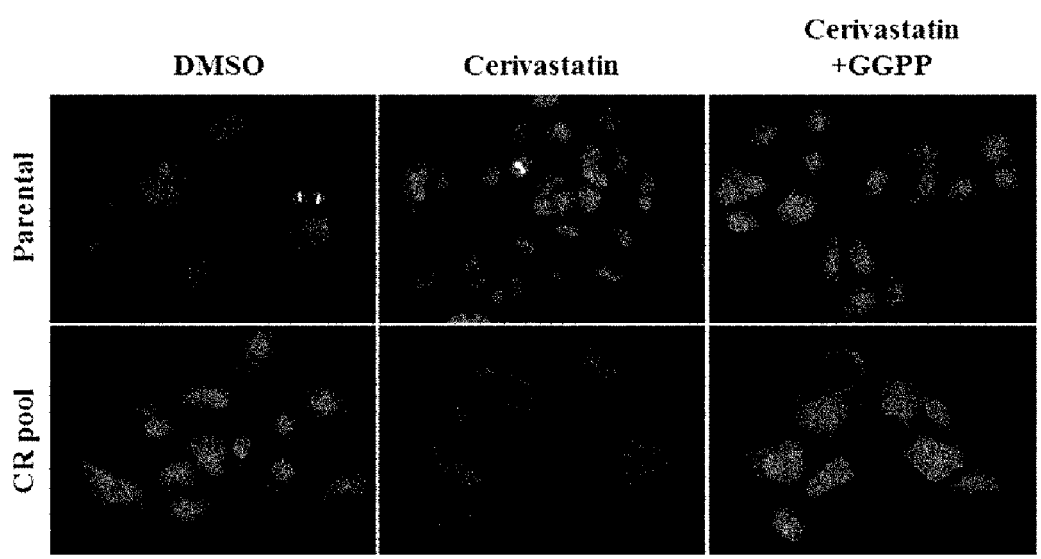

【FIG 8a】
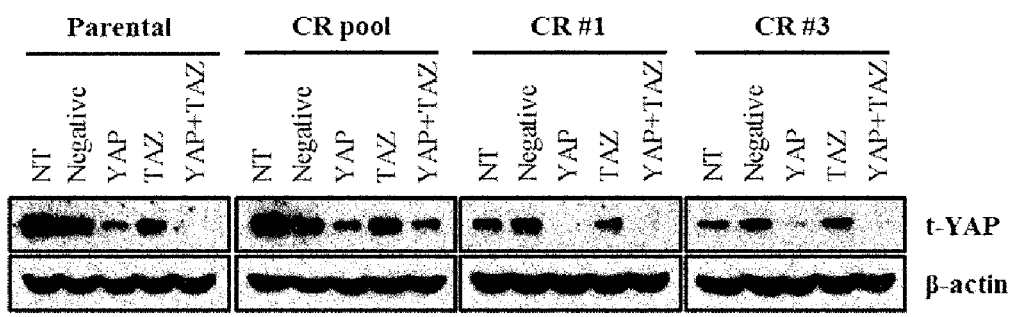
【FIG 8b】
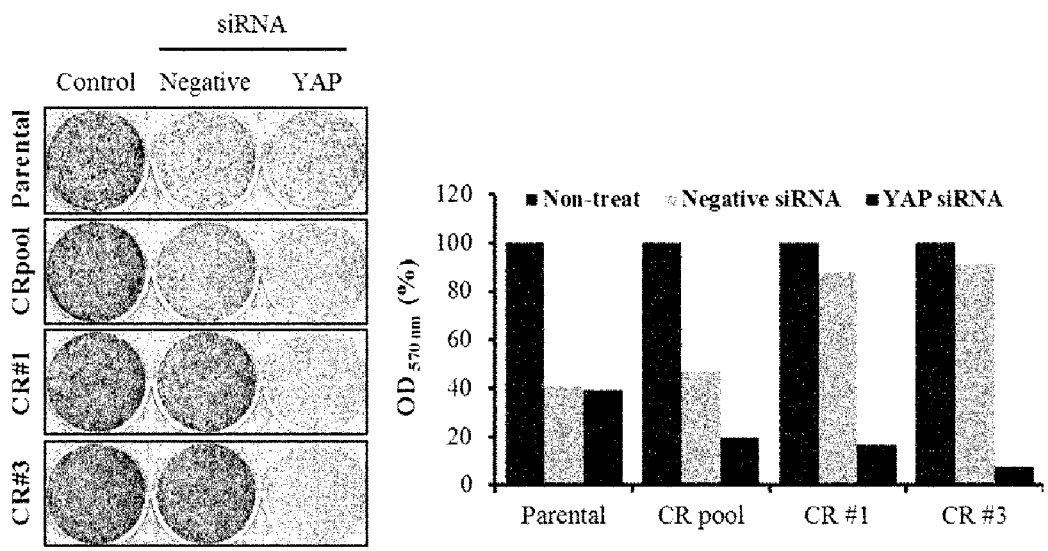

【FIG 9a】
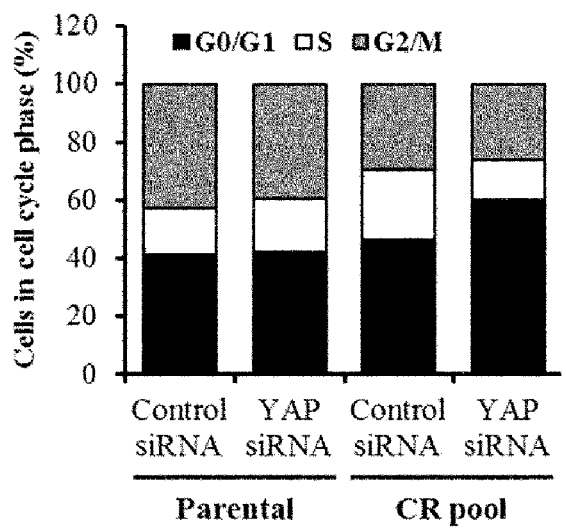
【FIG 9b】
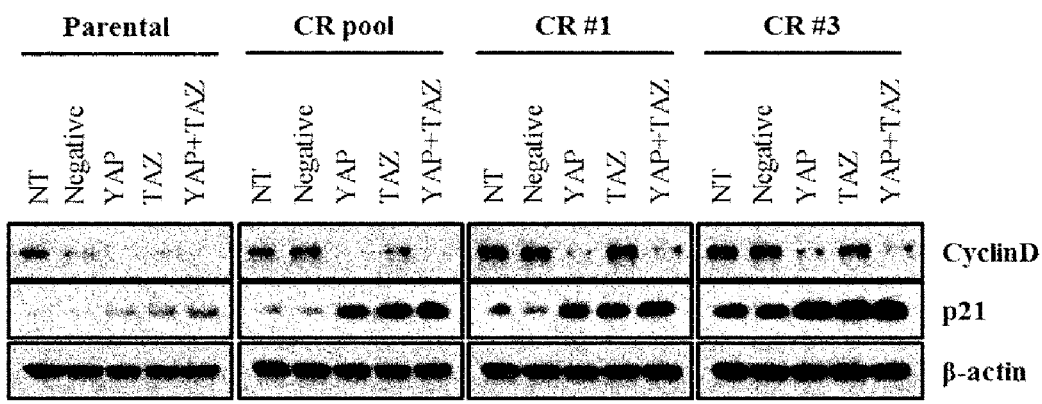

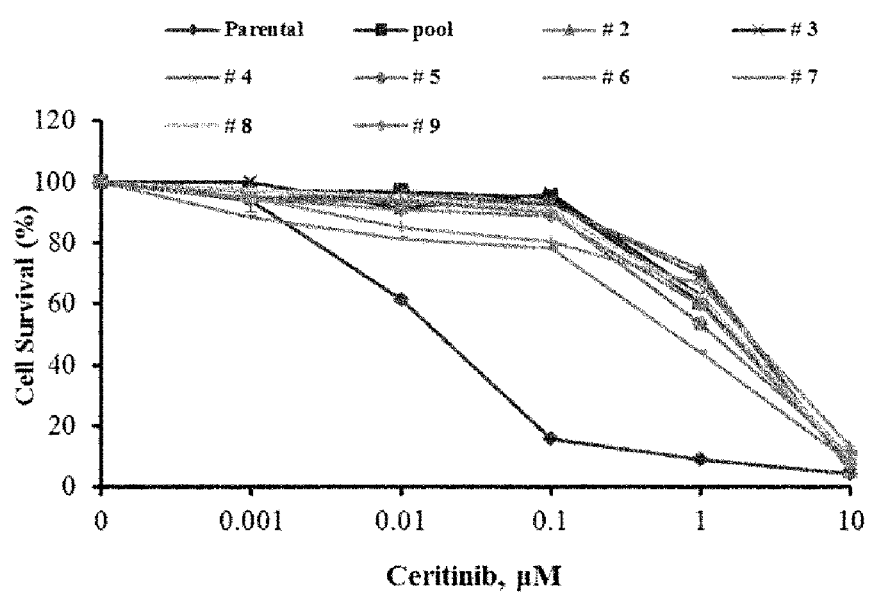
[FIG 10a]

[FIG 10b]
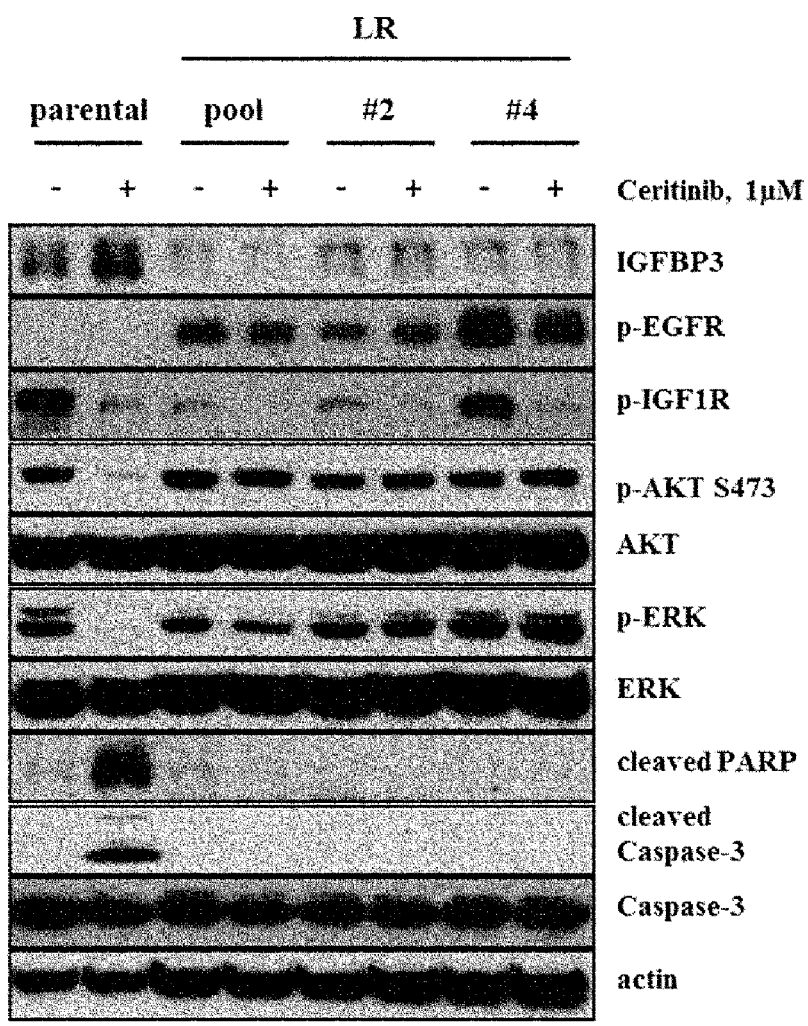

[FIG 11a]
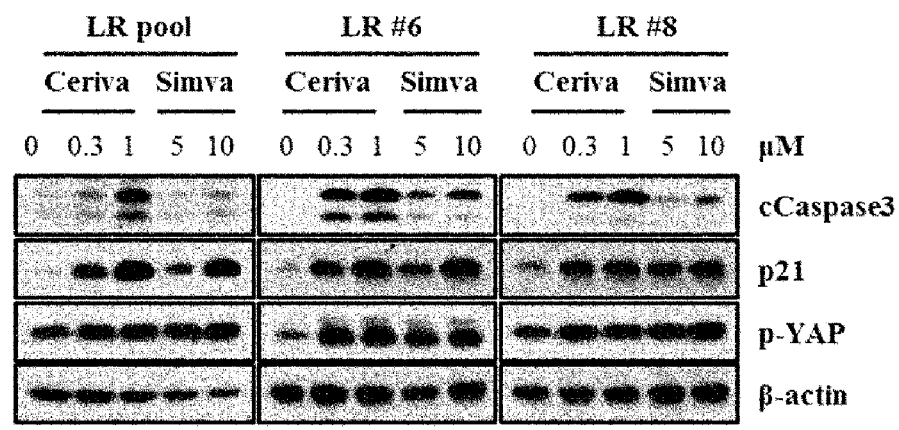
[FIG 11b]
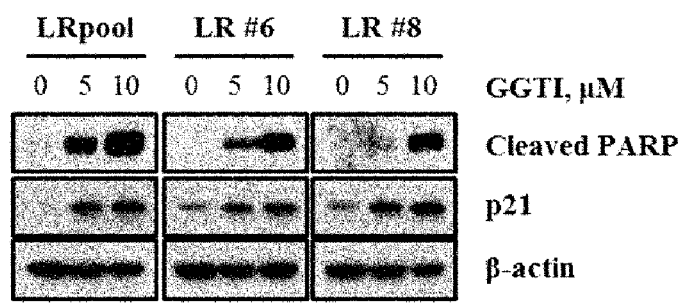

[FIG 11c]
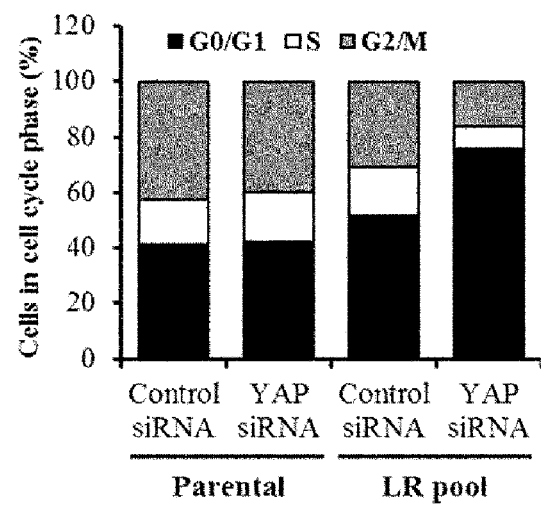
[FIG 11d]
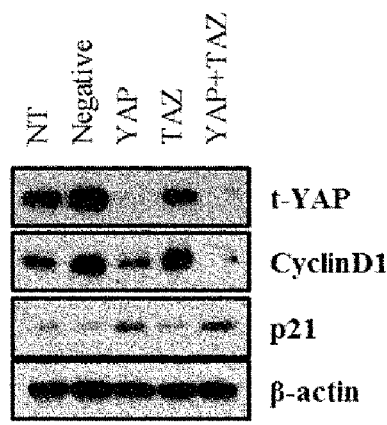

[FIG 12]
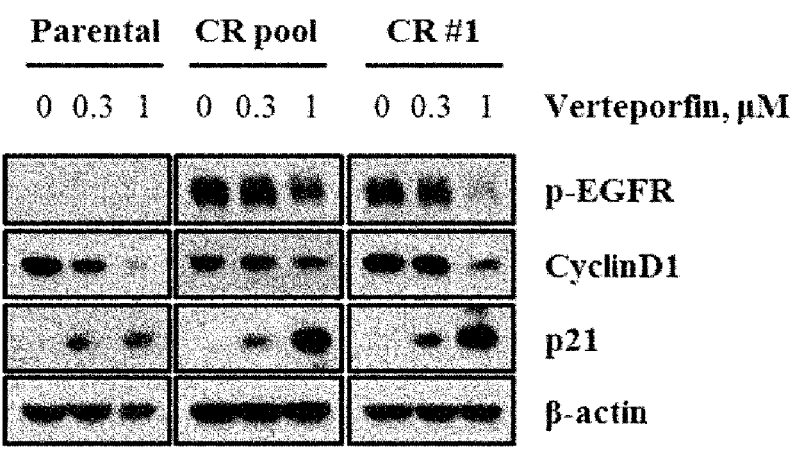
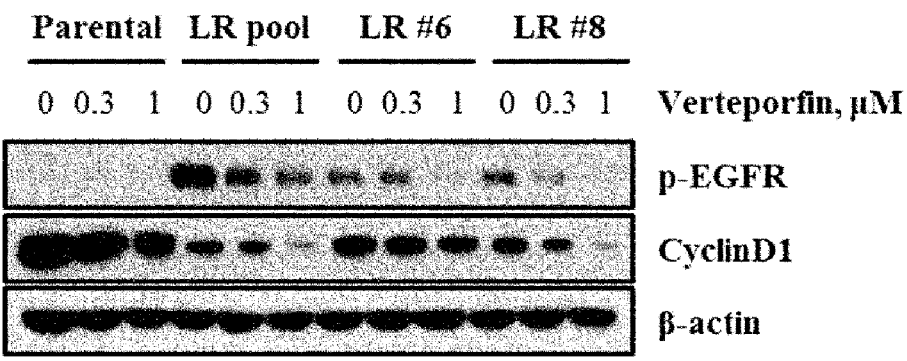

[FIG 13]
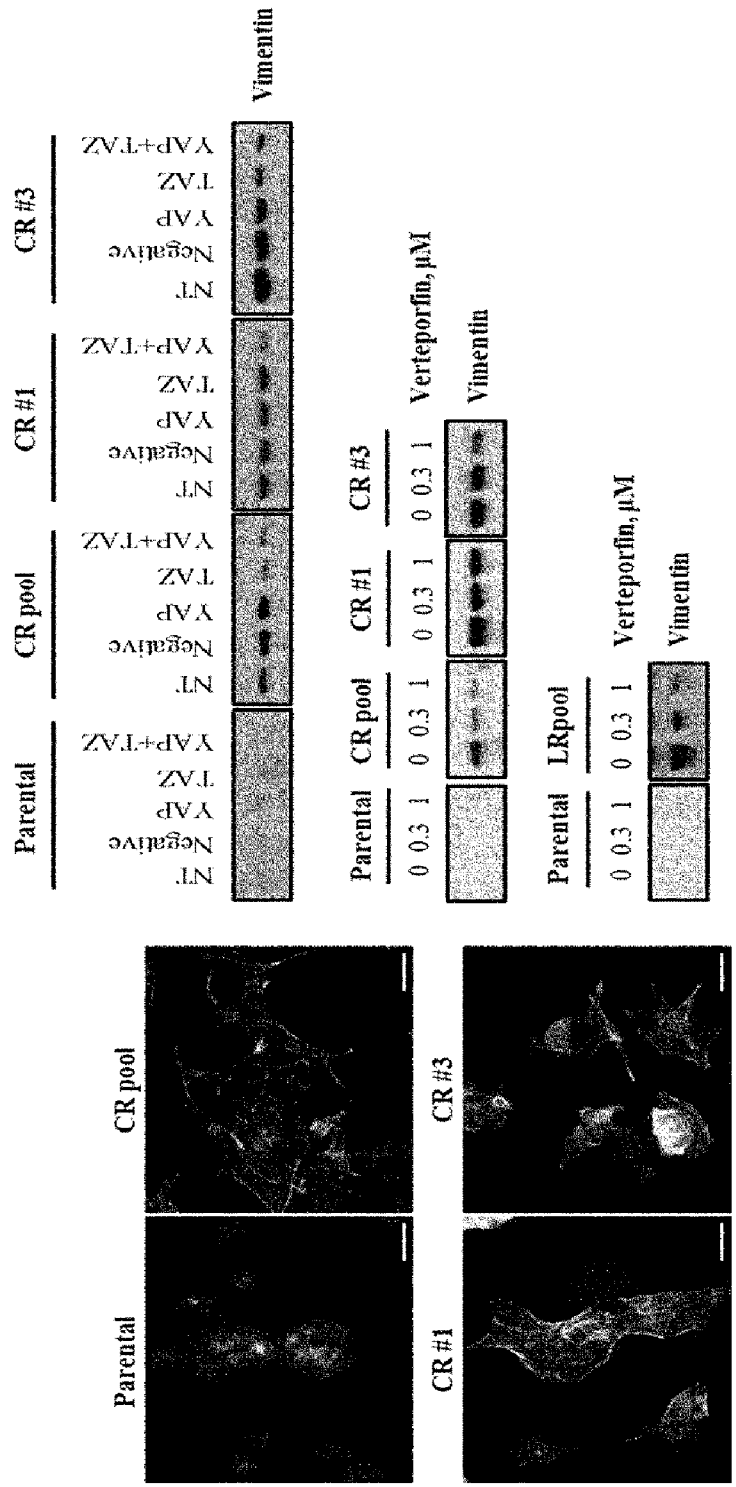

[FIG 14]
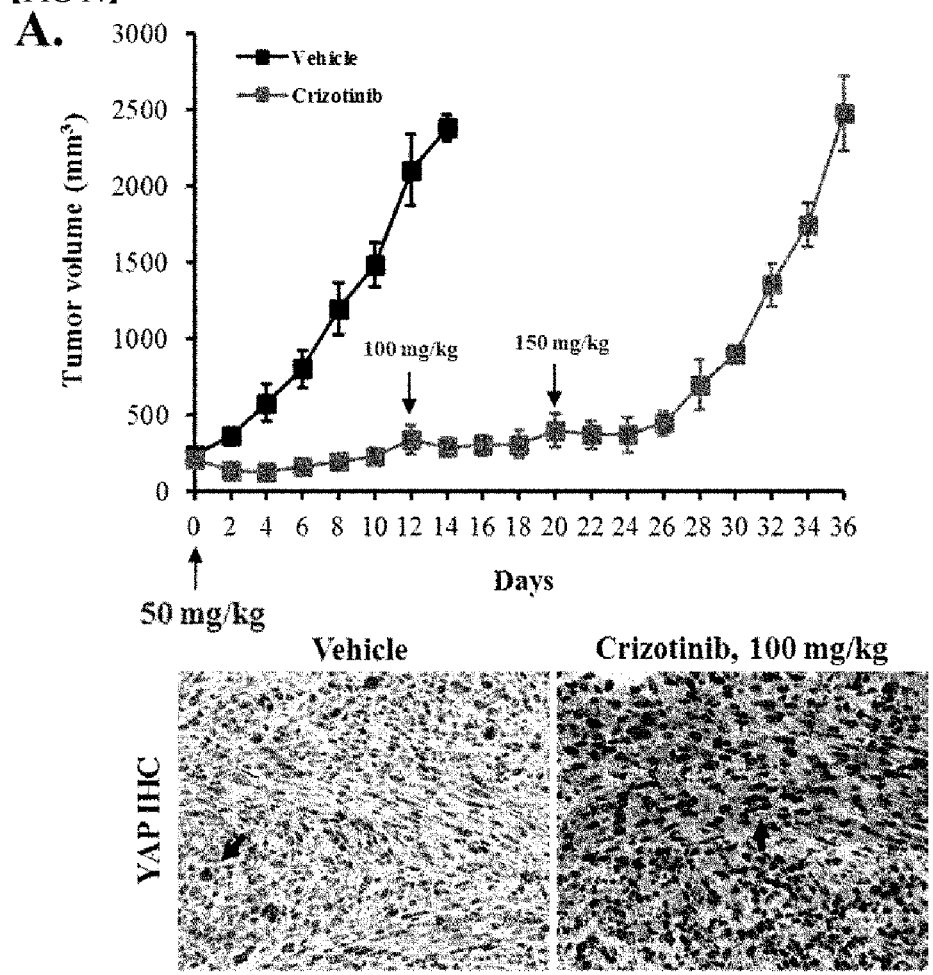
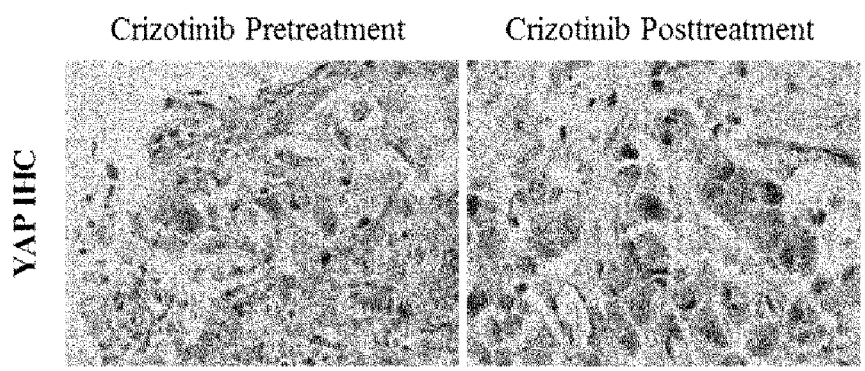

USE OF STATIN-BASED DRUG FOR TREATMENT OF EML4-ALK-POSITIVE NON-SMALL CELL LUNG CANCER PROGRESSING ON ALK INHIBITOR

CROSS-REFERENCE TO RELATED APPLICATION

This application is a Section 371 of International Application No. PCT/KR2017/000502, filed Jan. 13, 2017, which was published in the Korean language on Jul. 20, 2017, under International Publication No. WO 2017/123063 A1, which claims priority under 35 U.S.C. § 119(b) to Korean Patent Application No. 10-2016-0004510, filed on Jan. 14, 2016, the disclosures of which are incorporated herein by reference in their entireties.

BACKGROUND

1. Field of the Invention

The present invention relates to a pharmaceutical composition for treating EML4-ALK positive non-small cell lung cancer that has acquired resistance to an ALK inhibitor, including a statin-based drug and a method for providing information for selecting a drug for treatment of EML4-ALK positive non-small cell lung cancer when resistance to the ALK inhibitor is acquired.

2. Discussion of Related Art

A statin-based drug is a therapeutic agent for hyperlipidemia, and has been used as a lipid-lowering agent that suppresses biosynthesis of cholesterol by inhibiting HMG-CoA reductase. Such statin-based drugs exhibit their efficacies by inhibiting the activity of HMG-CoA which is an enzyme involved in a process in which HMG-CoA is converted into mevalonic acid, which is a rate-determining step (rate-limiting step) of biosynthesis of cholesterol in hepatocytes. Further, an intermediate (geranyl PP, farnesyl PP) produced in the process of synthesizing cholesterol plays a role in the cell signaling system by activating a Rho protein or Ros protein, and the statin-based drug has been reported to have an effect of blocking the signaling of such cells by blocking the synthesis of cholesterol.

Examples of the statin-based drug that has been used as a therapeutic agent for hyperlipidemia include simvastatin, lovastatin, atorvastatin, pravastatin, fluvastatin, rosuvastatin, pitavastatin, and the like. However, the statin-based drug has been recently reported to exhibit drug efficacy in addition to the application of lowering cholesterol. It has been revealed that the statin-based drug serves to expand blood vessels, regulate brain function, facilitate the synthesis of collagen, and proliferate blood vessel walls by directly acting even on cardiac arteries, and is also effective for the prevention of dementia, Alzheimer's disease, or the like.

Meanwhile, anaplastic lymphoma kinase (ALK) is a tyrosine kinase receptor, and plays an important role in the proliferation, growth and survival of cells via the Ras/Raf/MEK/ERK1/2 pathway, the Janus kinase/signal transducers and activators of transcription (JAK/STAT) pathway, and the phosphatidylinositol 3-kinase (PI3K)/Akt pathway. However, the overexpression of ALK leads to abnormal proliferation and growth of cancer cells.

Meanwhile, since it is known that the echinoderm microtubule-associated protein-like 4 (EML4)-ALK mutation of ALK plays an important role in abnormal proliferation of cancer cells in non-small cell lung cancer, studies and interests in anticancer treatment targeting ALK have been increased.

As a target therapeutic agent for such ALK, an ALK inhibitor such as crizotinib and ceritinib has been used, but when non-small cell lung cancer is treated through the ALK inhibitor, there is a problem in that lung cancer cell lines exhibiting resistance to the ALK inhibitor are generated in about one year or so.

Therefore, there is a need for studying and developing a new target therapeutic agent exhibiting therapeutic efficacy in a patient group with EML4-ALK positive non-small cell lung cancer that has acquired resistance to an ALK inhibitor.

SUMMARY OF THE INVENTION

An object of the present application is to provide a pharmaceutical composition exhibiting a therapeutic effect on EML4-ALK positive non-small cell lung cancer that has acquired resistance to an ALK inhibitor and a method for providing information for drug selection in order to solve the problem.

In order to achieve the object, the present invention provides a pharmaceutical composition for use in treatment of EML4-ALK positive non-small cell lung cancer that has acquired resistance to an ALK inhibitor, including a statin-based drug or a pharmaceutically acceptable salt thereof.

The present invention also provides a method for treating EML4-ALK positive non-small cell lung cancer that has acquired resistance to an ALK inhibitor, the method including: administering the pharmaceutical composition to a subject in need thereof.

The present invention also provides a method for providing information for selecting a drug for treatment of EML4-ALK positive non-small cell lung cancer that has acquired resistance to an ALK inhibitor, the method including: confirming whether resistance to the ALK inhibitor has been acquired in a patient with EML4-ALK positive non-small cell lung cancer, and providing the information so as to administer the statin-based drug for treatment of EML4-ALK positive non-small cell lung cancer when resistance to the ALK inhibitor has been acquired.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 illustrates a process of constructing a cell line that has acquired resistance to crizotinib, and FIG. 1A illustrates the cell survival rate of a non-small cell lung cancer cell line that has acquired resistance according to the concentration of crizotinib, FIG. 1B illustrates the cell survival rate of CR pool, CR #1, and CR #3, and FIG. 1C illustrates colony formation assay results;

FIG. 2 illustrates a result of analyzing the activity of the lower signaling pathway and the bypass signaling pathway of ALK for a cell line that has acquired resistance to crizotinib through an immunoblot;

FIG. 3A illustrates the cell survival rate after the treatment of the cell line that has acquired resistance to crizotinib with ceritinib, and FIG. 3B illustrates the cell survival rate after the treatment with gefitinib and afatinib;

FIG. 4A illustrates the cell survival rate according to a drug in order to blindly select a drug that suppresses the growth of cells by treating H3122CR pool cells with about 640 drugs from the FDA approved drug library, and FIG. 4B identifies antitumor efficacies of cerivastatin, simvastatin, and fluvastatin. FIG. 4C identifies antitumor efficacies of crizotinib and cerivastatin against lung cancer cell lines;

FIG. 5A illustrates a colony formation analysis result when a cell line that has acquired resistance to crizotinib is treated with cerivastatin, FIG. 5B identifies a cell cycle analysis according to the colony formation analysis result, and FIG. 5C identifies antitumor efficacies of cerivastatin and simvastatin through a western blot analysis method;

FIG. 6A is a result identifying the proliferation of cells by adding byproducts mediated by a mevalonate pathway to a cell line that has acquired resistance to crizotinib treated with cerivastatin, FIG. 6B is a result identifying the expression of p21, cleaved PARP, and cleaved caspase 3 during the treatment with GGPP through a western blot analysis, and FIG. 6C is a result identifying the expression of p21, cleaved PARP, and cleaved caspase 3 when GGTI-298 is treated;

FIGS. 7A and 7B identify the expression pattern of YAP when GGPP and GGRI-298 are treated, respectively through a western blot, and FIG. 7C illustrates whether YAP moves into the nucleus through an immunocytochemistry analysis;

FIG. 8A identifies the expression pattern of YAP after the expression of YAP/TAZ is deleted in the cell line resistant to crizotinib and the parental cells, and FIG. 8B identifies effects of the deletion of expression of YAP/TAZ on the proliferation of cells through a colony formation analysis;

FIG. 9A is a result of analyzing effects of the deletion of expression of YAP/TAZ on the cell cycle in the cell line resistant to crizotinib and the parental cells, and FIG. 9B identifies the expression pattern of cyclin D1 and p21 after the expression of YAP/TAZ is deleted through a western blot analysis;

FIG. 10A illustrates the cell survival rate according to the concentration of ceritinib in a cell line that has acquired resistance to ceritinib, and FIG. 10B illustrates a result of evaluating the activity of the lower signaling pathway and the bypass signaling pathway of ALK for a resistant cell line through an immunoblot analysis method;

FIG. 11A illustrates the expression pattern of cleaved caspase 3, p21, and YAP according to the concentration of cerivastatin and simvastatin in a cell line that has acquired resistance to ceritinib, and FIG. 11B identifies the expression pattern of cleaved PARP and p21 after GGRI is treated. FIGS. 11C and 11D illustrate a result of analyzing the cell cycle after the expression of YAP/TAZ is deleted and a result of identifying the expression pattern of YAP, cyclin D1, and p21 according to the analyzed result through a western blot analysis, respectively;

FIG. 12 is a result of identifying the degree of activity of EGFR after a cell line that has acquired resistance to crizotinib and a cell line that has acquired resistance to ceritinib are treated with verteporfin through a western blot analysis method;

FIG. 13 illustrates a result of identifying a change aspect in cell shape in an H3122 parental cell line and a cell line that has acquired resistance to crizotinib, and a result of analyzing the expression pattern of vimentin according to the deletion of YAP/TAZ and treatment with verteporfin through a western blot; and FIG. 14A illustrates a process of constructing a tumor tissue that has acquired resistance to crizotinib by identifying the change in tumor size while crizotinib is administered to an ALK-PDTX tissue by gradually increasing the dose of crizotinib, and FIG. 14B illustrates a result of identifying the expression of YAP in the constructed tumor tissue that has acquired resistance to crizotinib through an immunostaining method.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Hereinafter, the configuration of the present invention will be specifically described.

The present invention provides a pharmaceutical composition for use in treatment of EML4-ALK positive non-small cell lung cancer that has acquired resistance to an ALK inhibitor, including a statin-based drug or a pharmaceutically acceptable salt thereof.

In general, the statin-based drug has been used for the treatment of hyperlipidemia (disorder), but the pharmaceutical composition according to the present invention can exhibit therapeutic effects on non-small cell lung cancer of a patient that has acquired resistance to an ALK inhibitor among patients with EML4-ALK positive non-small cell lung cancer by including a statin-based drug.

Accordingly, the present invention provides a secondary medical use of a statin-based drug in treatment of ALK positive non-small cell lung cancer.

In the present invention, the statin-based drug may be any one selected from the group consisting of cerivastatin, rosuvastatin, simvastatin, atorvastatin, and fluvastatin, but is not limited thereto. In one specific example of the present invention, the statin-based drug may be cerivastatin.

In the present invention, the pharmaceutically acceptable salt of the statin-based drug refers to an organic or inorganic addition salt in which side effects caused by the salt do not reduce the beneficial efficacy of the statin-based drug at a concentration which has an effective action which is relatively non-toxic and innocuous to a patient. For example, a pharmaceutically acceptable salt may be an acid addition salt formed by using an organic acid or an inorganic acid, the organic acid includes, for example, acetic acid, propionic acid, lactic acid, butyric acid, isobutyric acid, trifluoroacetic acid, malic acid, maleic acid, malonic acid, fumaric acid, succinic acid, monoamide succinate, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzensulfonic acid, p-toluenesulfonic acid, and methanesulfonic acid, and the inorganic acid includes, for example, hydrochloric acid, bromic acid, sulfuric acid, phosphoric acid, nitric acid, carbonic acid, and boric acid. Preferably, the pharmaceutically acceptable salt may be in the form of a hydrochloric acid salt or an acetic acid salt. Further, the pharmaceutically acceptable salt may be an alkali metal salt (a sodium salt, a potassium salt, and the like), an alkaline earth metal salt (a calcium salt, a magnesium salt), and the like.

In the present invention, the "patient with EML4-ALK positive non-small cell lung cancer" refers to a patient in which a mutation of the ALK gene occurs among patients with non-small cell lung cancer. The mutation of the ALK gene may be formed from the fusion of the EML4 and ALK genes. The gene in which fusion occurs causes cancer by expressing EML4-ALK.

In the present invention, the "ALK inhibitor" refers to a drug which suppresses the kinase activity of EML4-ALK as a drug exhibiting therapeutic effects for the patient with EML4-ALK positive non-small cell lung cancer.

In the present invention, the "EML4-ALK positive non-small cell lung cancer that has acquired resistance to an ALK inhibitor" refers to a case of having acquired resistance to an ALK inhibitor against EML4-ALK positive non-small cell lung cancer in which a mutation has occurred from the fusion of EML4 and ALK in the non-small cell lung cancer.

In one specific example, the EML4-ALK positive non-small cell lung cancer that has acquired resistance to an ALK inhibitor may be in a state where the Yes-associated protein (YAP) is activated.

According to the present invention, the activation of the YAP is a mechanism of acquiring new resistance identified from a cell line having resistance to an ALK inhibitor in an EML4-ALK positive non-small cell lung cancer cell line, and it has been revealed that the YAP is activated by geranylgeranylation to cause proliferation of cancer cells by activating the EGFR signaling pathway.

Further, according to the present invention, a statin-based drug has an excellent effect of suppressing the activation of the YAP of non-small cell lung cancer cells, and thus can be usefully used for the treatment of non-small cell lung cancer.

The patient with EML4-ALK positive non-small cell lung cancer may include a patient having resistance to one or more ALK inhibitors selected from the group consisting of crizotinib, ceritinib, alectinib, brigatinib, and entrectinib.

According to the present invention, a statin-based drug or a pharmaceutically acceptable salt thereof can be usefully used for the prevention and treatment of EML4-ALK positive non-small cell lung cancer that has acquired resistance to an ALK inhibitor.

In the present invention, a subject may be a human in need of the prevention and/or treatment of EML4-ALK positive non-small cell lung cancer that has acquired resistance to an ALK inhibitor. The subject also includes a patient or a normal person.

Thus, the present invention provides a method for treating EML4-ALK positive non-small cell lung cancer that has acquired resistance to an ALK inhibitor, the method including: administering a statin-based drug or a pharmaceutically acceptable salt thereof to a subject in need thereof.

Further, the present invention provides a method for providing information for selecting a drug for treatment of EML4-ALK positive non-small cell lung cancer that has acquired resistance to an ALK inhibitor, the method including: confirming whether resistance to the ALK inhibitor has been acquired in a patient with EML4-ALK positive non-small cell lung cancer, and providing the information so as to administer the statin-based drug for treatment of EML4-ALK positive non-small cell lung cancer when resistance to the ALK inhibitor has been acquired.

In one specific example, all the contents described above on the statin-based drug, the ALK inhibitor, and the patient with EML4-ALK positive non-small cell lung cancer may be applied as they are or mutatis mutandis.

In the present invention, in the process of confirming whether resistance to the ALK inhibitor, it is possible to say that resistance to an ALK inhibitor has been acquired when extremely low sensitivity to the ALK inhibitor administered to treat non-small cell lung cancer in a patient with non-small cell lung cancer is exhibited, and as a result, symptoms of cancer do not exhibit improvement, alleviation, reduction or treatment symptoms, or the cancer exhibits progression even after the ALK inhibitor is administered. A means of identifying the progression of non-small cell lung cancer is not particularly limited as long as the means can be all the means of imaging and identifying the occurrence of cancer, for example, a means capable of identifying the occurrence of cancer through an imaging technique such as computed tomography (CT), magnetic resonance imaging (MRI), ultrasonography, X-ray imaging, mammography, PET scanning, radionuclide scanning, and bone scanning.

In addition, in the present invention, whether resistance to the ALK inhibitor has been acquired can be confirmed at the cellular level. In one specific example, it is possible to confirm whether resistance to the ALK inhibitor has been acquired using an analysis method such as an MTT assay and a colony formation assay for a cell line that has acquired resistance by continuously treating an EML4-ALK positive non-small cell lung cancer cell line exhibiting responsiveness to the ALK inhibitor with the ALK inhibitor, but the method is not limited thereto.

The method for providing information for drug selection according to the present invention may include: further confirming whether YAP is activated in a patient who has acquired resistance to the ALK inhibitor among the patients with EML4-ALK positive non-small cell lung cancer.

In one specific example, the confirming of whether YAP is activated may additionally include: confirming whether YAP is expressed by detecting a YAP protein. The detecting of the YAP protein may include detecting a YAP protein in a cell nucleus from a living tissue of a patient with non-small cell lung cancer that has acquired resistance to an ALK inhibitor through an analysis method such as immunohistochemistry and a western blot.

Accordingly, the pharmaceutical composition of the present invention may include a statin-based drug for treatment of EML4-ALK positive non-small cell lung cancer that has acquired resistance to an ALK inhibitor in which YAP is activated.

The pharmaceutical composition of the present invention may include a pharmaceutically acceptable carrier. In the present invention, the term "pharmaceutically acceptable carrier" refers to a carrier or diluent that does not significantly stimulate an organism and does not inhibit the biological activity or properties of an administered ingredient. The pharmaceutically acceptable carrier in the present invention may be used by mixing a saline solution, sterilized water, Ringer's solution, a buffered saline solution, a dextrose solution, a maltodextrin solution, glycerol, ethanol, and one ingredient from these ingredients, or one or more among these ingredients, and may be formulated in the form of an injection suitable for infusion into a tissue or an organ by adding other typical additives such as an antioxidant, a buffer, and a bacteriostatic agent, if necessary. Furthermore, the pharmaceutically acceptable carrier may also be formulated as a dry preparation (particularly, a lyophilized preparation) which may be an injectable solution by adding an isotonic sterile solution, or sterilized water or a physiological saline solution in some cases. Further, a target organ specific antibody or another ligand may be used in combination with the carrier so as to specifically act on a target organ.

In addition, preferably, the composition of the present invention may additionally include a filler, an excipient, a disintegrating agent, a binding agent, a lubricant, and the like. Furthermore, the composition of the present invention may be formulated using a method publicly known in the art so as to provide a rapid, sustained or delayed release of an active ingredient after administration to mammals.

In the present invention, the term "administration" refers to administration of the composition of the present invention to a patient by any appropriate method, and for the route of administration of the composition of the present invention, the composition of the present invention may be administered via various routes of oral or parenteral administration, which may reach a target tissue. The route of administration may be intraperitoneal administration, intravenous administration, intramuscular administration, subcutaneous administration, intradermal administration, oral administration, topical administration, intranasal administration, intrapulmonary administration, and rectal administration, but is not limited thereto.

In the present specification, "effective amount" refers to an amount required to delay or completely stop the onset or progression of a specific disease to be treated. In the present invention, the composition may be administered in a pharmaceutically effective amount. It is obvious to a person skilled in the art that a suitable total usage amount per day may be determined by a doctor within the scope of sound medical judgment.

For the purpose of the present invention, it is preferred that a specific therapeutically effective amount for a specific patient is differently applied depending on various factors including the type and extent of a response to be achieved, a specific composition including whether other formulations are used according to the case, the age, body weight, general health status, gender, and diet of the patient, the time of administration, the route of administration, the secretion rate of the composition, the period of treatment, a drug in combination with or concurrently with the specific composition and similar factors well known in the medical field.

The benefits and features of the present invention, and the methods of achieving the benefits and features will become apparent with reference to experimental examples and preparation examples to be described below in detail. However, the present invention is not limited to the experimental examples and the preparation examples to be disclosed below and may be implemented in various other forms, and the present invention is provided for rendering the disclosure of the present invention complete and for fully representing the scope of the present invention to a person with ordinary skill in the art to which the present invention pertains.

Preparation Example 1. Construction of Non-Small Cell Lung Cancer Cell Line that has Acquired Resistance to Crizotinib A non-small cell lung cancer cell line that acquired resistance (named H3122 CR pool) was constructed by continuously culturing a surviving H3122 cell line in a medium supplemented with 1 µM crizotinib while continuously increasing the concentration of crizotinib (Pfizer Inc., US) which is a first-generation ALK inhibitor, starting from 0.01 µM to 1 µM in a cell line of H3122 (referred to as Parental), which is an EML4-ALK positive non-small cell lung cancer cell line. It was confirmed whether resistance to crizotinib had been acquired by constructing 10 H3122CR clonal cell lines (referred to as H3122CR #1 to #10) from the H3122 CR pool through a single cell isolation to perform an MTT assay and a colony formation assay on the 10 H3122CR clones. Subsequently, studies on the mechanism of acquiring resistance to an ALK inhibitor in the Experimental Examples were carried out by representatively using CR pool, CR #1, and CR #3. The process of constructing a cell line that has acquired resistance is illustrated in FIG. 1. FIG. 1A illustrates the cell survival rate of a non-small cell lung cancer cell line that has acquired resistance according to the concentration of crizotinib, FIG. 1B illustrates the cell survival rate of CR pool, CR #1, and CR #3, and FIG. 1C illustrates colony formation assay results.

Experimental Example 1. Evaluation of Activity of Lower Signaling Pathway of ALK in Cell Line that has Acquired Resistance to Crizotinib For the cell line constructed in Preparation Example 1, the activity of the lower signaling pathway and the bypass signaling pathway of ALK was evaluated through an immunoblot analysis method. The results are illustrated in FIG. 2.

As illustrated in FIG. 2, in the case of the parental cell line, although the activation of the ALK, AKT, and ERK was all suppressed by 1 µM crizotinib, when CR pool, CR #1, and CR #3 were treated with 1 µM crizotinib, the activity of ERK was maintained and the activity of AKT was reduced, but the phosphorylation basal levels of CR #1 and CR #3 were much higher than that of Parental.

Recently, since it has been reported that EGFR is activated by a mechanism of acquiring resistance to an ALK inhibitor, this matter was examined, as a result of confirming whether EGFR was activated in a resistant cell line which the present research team constructed, EGFR expression and activation were both increased as compared to the parental cell line, and were not inhibited by a high concentration of crizotinib.

More interestingly, the expression of ALK in CR pool, CR #1, and CR #3 was much lower than that of the parental cells, and although a secondary mutation (L1152R, C1156Y, F1174, L1196M, L1198F, G1202R, S1206Y, and G1269A) in the ALK kinase domain, which had been reported to be associated with induction of resistance to an ALK inhibitor, had been identified by Sanger sequencing, it was confirmed that mutations in these resistant cell lines did not occur.

Experimental Example 2. Experiment for Overcoming Resistance of Cell Line that has Acquired Resistance to Crizotinib After the cell line constructed in Preparation Example 1 was treated with ceritinib which is an ALK inhibitor and gefitinib and afatinib which are EGFR inhibitors, the cell survival rate was identified. The results are illustrated in FIG. 3. FIG. 3A illustrates the cell survival rate after the treatment of the cell line with ceritinib, and FIG. 3B illustrates the cell survival rate after the treatment with gefitinib and afatinib.

As illustrated in FIG. 3, it could be confirmed that even though the cell line was treated with ceritinib which is a second-generation ALK inhibitor or ALK was knocked down, the proliferation of the cell line that had acquired resistance was not suppressed. This confirmation coincides with the significance of the result that the dependency on ALK is excluded in the cell line resistant to crizotinib, and the secondary mutation does not occur. Further, even though the expression and activity of EGFR in the cell line that had acquired resistance was increased, it was confirmed that the proliferation of the cell line that had acquired resistance could not be suppressed by gefitinib and afatinib which are EGFR inhibitors.

Accordingly, the above results signify that the cell lines that have acquired resistance to crizotinib, which were constructed by the present research team, are non-dependent on ALK and acquire resistance to an ALK inhibitor through a new mechanism other than the acquisition of a second gatekeeper mutation. Moreover, it is suggested that the activity of EGFR may not be a main target for overcoming resistance.

Experimental Example 3. Drug Selection and Antitumor Efficacy of Drug

1) Selection Experiment for Drug Exhibiting Antitumor Efficacy in Cell Line That Has Acquired Resistance to Crizotinib and Evaluation of Antitumor Efficacy of Statin-Based Drug In order to elucidate a new mechanism other than the resistance mechanism of an ALK inhibitor, which was already reported in consideration of the diversity of the resistance mechanism for one drug, after H3122CR pool cells were treated with about 640 drugs from the FDA approved drug library purchased from Enzo Life Sciences, Inc. at a concentration of 1 μM for 72 hours by applying a drug repositioning (new drug discovery) strategy which is one method of the new drug developments of developing new medicinal uses of drugs which are already commercially available or failed to be industrialized for reasons in addition to safety at the clinical stage, a drug for inhibiting the growth of cells was blindly selected.

The results are illustrated in FIG. 4A. FIG. 4B illustrates antitumor efficacies of crizotinib, cerivastatin, simvastatin, and fluvastatin, FIG. 4C illustrates antitumor efficacies of crizotinib and cerivastatin against lung cancer cell lines.

As illustrated in FIG. 4, as a result of identifying the selected drugs, drugs which all suppressed the growth of H3122 parental cells and H3122 CR pool cells are cytotoxic anticancer agents mostly used in chemotherapy, such as anthracycline anticancer agents including doxorubicin, vinca alkaloids, and docetaxel, and the like, and these drugs were excluded from candidate drugs because the drugs are not likely to be used as a target therapeutic agent and exhibit very slight therapeutic effects in a clinical setting when acquiring resistance to ALK positive non-small cell lung cancer and an ALK inhibitor. When a drug highly likely to be used as a target therapeutic agent was selected, the present research team had interestingly focused on statin-based cerivastatin which is an HMG-CoA reductase suppressor exhibiting effects of inhibiting the proliferation of cells specific to a resistant cell line rather than parental cells. In addition, the antitumor efficacies of statin-based drugs (simvastatin, fluvastatin, rosuvastatin, and atorvastatin) other than cerivastatin were evaluated, and it was confirmed that all the statin-based drugs specifically exhibited antitumor efficacies against a cell line resistant to the ALK inhibitor. The statin-based drugs have been recently reported to have effects of suppressing the proliferation of cancer cells and the metastasis of cancer, so that based on these results, it was determined that the function of the statin-based drug with respect to the mechanism of acquiring resistance to an ALK inhibitor needed to be elucidated.

2) Evaluation of Antitumor Efficacy of Cerivastatin in Cell Line that has Acquired Resistance to Crizotinib Furthermore, the antitumor efficacy of cerivastatin in a cell line resistant to an ALK inhibitor was once again identified through colony formation, a cell cycle analysis, and a western blot analysis method in addition to MTT, and the results are illustrated in FIG. 5. FIG. 5A illustrates a colony formation analysis result of cerivastatin, FIG. 5B illustrates a cell cycle analysis, and FIG. 5C is a result identifying antitumor efficacies of cerivastatin and simvastatin through a western blot analysis method.

As illustrated in FIG. 5, it was confirmed that cerivastatin specifically blocked colony formation only in a cell line that had acquired resistance to crizotinib, strongly induced G1 arrest in the cell cycle, and concentration-dependently increased the expression of p21 which is a CDK inhibitor protein (CIP/KIP family) known as a G1 arrest-inducing protein and the expression of cleaved PARP and cleaved caspase 3, which are apoptosis-related proteins.

3) Identification of Action Mechanism of Cerivastatin in Cell Line that has Acquired Resistance to Crizotinib in Mevalonate Pathway A statin-based drug is a suppressor of HMG-CoA reductase which is an enzyme converting 3-hydroxy-3-methylglutaryl coenzyme A (HMG-CoA) into mevalonic acid in the mevalonate pathway, and is known as a cholesterol-lowering agent, but is known to affect various intracellular signaling processes by suppressing the production of isoprenoids (Farnesyl pyrophosphate; FPP, Geranylgeranyl pyrophosphate; GGPP) acting as a substrate for isoprenylation of a target protein among final byproducts of the mevalonate pathway in addition to cholesterol. Thus, after the present research team treated H3122 parental, CR pool, CR #1, and CR #3 cell lines with cerivastatin in order to see which one of the byproducts mediated by the mevalonate pathway is involved in acquiring resistance to an ALK inhibitor, the proliferation of cells was identified after mevalonate, GGPP, FPP, and squalene, which are byproducts of each step, were each added. The results are illustrated in FIG. 6A. FIG. 6B illustrates a result identifying the expression of p21, cleaved PARP, and cleaved caspase 3 when GGPP is treated, through a western blot analysis, and FIG. 6C illustrates a result identifying the expression of p21, cleaved PARP, and cleaved caspase 3 when GGTI-298 is treated.

As illustrated in FIG. 6, the proliferation of cells suppressed by cerivastatin in the CR pool, CR #1, and CR #3 cell lines was each restored by mevalonate and GGPP, and the addition of FPP and squalene did not have any effect. Furthermore, through a western blot analysis, the expression of p21, cleaved PARP, and cleaved caspase 3 increased by cerivastatin was again decreased by GGPP. In order to more clearly elucidate this, when GGTI-298, which is a geranylgeranyl transferase inhibitor, was treated, the expression of PARP, caspase 3, and p21 was GGTI-298 concentration dependently induced in the resistant cell lines. Through the results, it can be confirmed that the restoration by mevalonate is a result again proving and showing the antitumor efficacy of cerivastatin, and it can be seen that the restoration by GGPP presents the possibility that the mechanism of acquiring resistance to an ALK inhibitor may be caused by geranylgeranylation affecting various signaling systems in the cells rather than a cholesterol synthesis pathway mediated by the mevalonate pathway.

Experimental Example 4. Elucidation of Function of YAP in Cell Line that has Acquired Resistance to Crizotinib 1) Correlation of Cerivastatin with YAP Activity with Respect to Antitumor Efficacy YAP is accumulated in the nucleus to form a complex with TEAD when phosphorylation is suppressed, and is known as an oncogene which promotes the excessive proliferation of cancer cells and the metastasis of cancer by inducing the expression of a gene associated with cancer. In addition, YAP as a transcription factor has been reported to be involved even in the expression of EGFR and an EGFR ligand. Recently, it has been reported that the mevalonate pathway which is an important mechanism in cancer cell metabolism regulates YAP activity, and particularly, geranylgeranylation may directly affect YAP activity. Accordingly, the expression pattern of YAP and whether YAP moves into the nucleus were compared in the H3122 parental cells and the H3122 CR cell line through a western blot and immunocytochemistry in order to see whether the antitumor efficacy of cerivastatin is associated with the activation of YAP in a cell line that has acquired resistance to crizotinib. The results are illustrated in FIG. 7. FIGS. 7A and 7B identify the expression pattern of YAP when GGPP and GGRI-298 are treated, respectively through a western blot, and FIG. 7C illustrates whether YAP moves into the nucleus through an immunocytochemistry analysis.

As illustrated in FIG. 7, in the resistant cell line, the expression of YAP was much higher and the phosphorylation of YAP was lower compared to the H3122 parental cells, but when the treatment with cerivastatin was performed, the phosphorylation of YAP was increased, and when GGPP, which is a byproduct of the mevalonate signal, was added together, the phosphorylation was again reduced. In addition, when the treatment with GGTI, which is a suppressor of geranylgeranylation, was performed, it was confirmed that the activation was decreased by increasing the phosphorylation of YAP as with cerivastatin. It can be seen that in the cell line resistant to crizotinib, the activity of YAP is specifically increased, and is regulated by cerivastatin/GGTI. Further, through cell fluorescence staining, it was confirmed that only in the resistant cell line, the expression of YAP was strongly stained in the nucleus, and it was observed that the expression of YAP was suppressed by cerivastatin, and the YAP again moved into the nucleus. Based on the result, the possibility of YAP as a mechanism of acquiring resistance to an ALK inhibitor was identified.

2) Verification of YAP as Resistance-Inducing Factor in Cell Line that has Acquired Resistance to Crizotinib In order to elucidate the function of YAP in a cell line that has acquired resistance to crizotinib, after the expression of YAP/TAZ was deleted by using siRNAs in both the cell line resistant to crizotinib and the parental cells, colony formation and the cell cycle were identified. The results are illustrated in FIGS. 8 and 9. FIG. 8A identifies the expression pattern of YAP after the expression of YAP/TAZ is deleted in the cell line resistant to crizotinib and the parental cells, and FIG. 8B identifies effects of the deletion of expression of YAP/TAZ on the proliferation of cells through a colony formation analysis. FIG. 9A is a result of analyzing effects of the deletion of expression of YAP/TAZ on the cell cycle in the cell line resistant to crizotinib and the parental cells, and FIG. 9B identifies the expression pattern of cyclin D1 and p21 after the expression of YAP/TAZ is deleted through a western blot analysis.

As illustrated in FIG. 8, even though YAP was deleted in the H3122 parental cells, colony formation was not affected, but when YAP was deleted in the cell line resistant to crizotinib, colony formation was strongly suppressed. In addition, as illustrated in FIG. 9, it was confirmed that the deletion of YAP increased the expression of p21 as with cerivastatin, and G1 arrest was induced in the cell cycle while decreasing the expression of cyclin D1. Through the results, it was confirmed that the regulation of the YAP activity by cerivastatin was likely to overcome acquired resistance to crizotinib in EML4-ALK positive non-small cell lung cancer.

Preparation Example 2. Construction of NSCLC Cell Line that has Acquired Resistance to Ceritinib A non-small cell lung cancer cell that has acquired resistance to ceritinib was constructed by continuously increasing the concentration of ceritinib (LDK378) (Novartis, Co., Ltd., Switzerland), which is a second-generation ALK inhibitor in the H3122 cell line in the same manner as in Preparation Example 1 (named H3122 LRpool).

Experimental Example 5. Evaluation of Activity of Lower Signaling Pathway of ALK in Cell Line that has Acquired Resistance to Ceritinib It was confirmed whether resistance to ceritinib was acquired by constructing 9 H3122LR clonal cell lines (named H3122LR #1 to #9) through single cell isolation from the H3122 LRpool prepared in Preparation Example 2 to carry out an MTT assay on the 9 H3122LR clones. Subsequently, studies on the mechanism of acquiring resistance to an ALK inhibitor in the Experimental Examples were carried out by representatively using pool, LR #4, and LR8#3. Further, for the cell line resistant to ceritinib, the activity of the lower signaling pathway and the bypass signaling pathway of ALK was evaluated through an immunoblot analysis method. The results are illustrated in FIG. 10. FIG. 10A illustrates the cell survival rate according to the concentration of ceritinib in a cell line that has acquired resistance to ceritinib, and FIG. 10B illustrates a result of evaluating the activity of the lower signaling pathway and the bypass signaling pathway of ALK for a resistant cell line through an immunoblot analysis method.

As illustrated in FIG. 10, the activity of EGFR was also increased in the cell line resistant to ceritinib in the same manner as in the cell line resistant to crizotinib, and the activities of AKT and ERK were not suppressed by ceritinib.

Experimental Example 6. Identification of Functions of Cerivastatin and YAP in Cell Line that has Acquired Resistance to Ceritinib In the cell line that has acquired resistance to crizotinib, the functions of cerivastatin and YAP were identified through a western blot and cell cycle analyses. The results are illustrated in FIG. 11. FIG. 11A illustrates the expression pattern of cleaved caspase 3, p21, and YAP according to the concentration of cerivastatin and simvastatin in a cell line acquiring resistance to ceritinib, and FIG. 11B identifies the expression pattern of cleaved PARP and p21 after GGRI is treated. FIGS. 11C and 11D illustrate a result of analyzing the cell cycle after the expression of YAP/TAZ is deleted and a result of identifying the expression pattern of YAP, cyclin D1, and p21 according to the analyzed result through a western blot analysis, respectively.

As illustrated in FIG. 11, it was confirmed that when the cell line resistant to ceritinib was treated with cerivastatin and simvastatin, which are statin-based drugs, in the same manner as in the cell line resistant to crizotinib, the expression of p21, which is a CDK inhibitor protein (CIP/KIP family) known as a G1 arrest-inducing protein and the expression of cleaved caspase 3, which is an apoptosis-related protein were concentration-dependently increased, and YAP activity was suppressed by inducing the phosphorylation of YAP. Further, even when GGTI-298, which is a geranylgeranyl transferase inhibitor, was treated, the expression of PARP and p21 was GGTI-298 concentration-dependently induced in the resistant cell lines. Furthermore, it was confirmed that when YAP was deleted, the expression of p21 was increased, and G1 arrest was induced in the cell cycle while decreasing the expression of cyclin D1. Through the results, it was confirmed that even in the mechanisms of acquiring resistance to crizotinib, which is a first-generation ALK inhibitor, and ceritinib, which is a second-generation ALK inhibitor, it is important to regulate YAP activity by cerivastatin.

Experimental Example 7. Observation of EGFR Activity Ability of Verteporfin

After the cell line that has acquired resistance to crizotinib was treated with verteporfin, the activity degree of EGFR was identified through a western blot analysis method. The results are illustrated in FIG. 12.

As illustrated in FIG. 12, it could be confirmed that verteporfin serves to suppress the transcriptional activity of the target factors of YAP/TAZ by blocking the binding of YAP and TAZ, and when pretreatment with verteporfin was performed, the activity of EGFR was concentration-dependently suppressed in the cell line that has acquired resistance to an ALK inhibitor.

Experimental Example 8. Identification of Function of YAP Against Cancer Metastasis Ability A change aspect in cell shape in an H3122 parental cell line and a cell line that has acquired resistance to crizotinib was identified, and the expression pattern of vimentin according to the deletion of YAP/TAZ and treatment with verteporfin was analyzed through a western blot. The results are illustrated in FIG. 13.

As illustrated in FIG. 13, it was observed that most of the H31122 parental cell line inherently has a round shape and proliferates while forming a colony, and to the cell line that has acquired resistance to crizotinib, a change in cell shape occurred from an original cell form having a round shape to a long form having a protrusion such as a pseudopodium. This observation suggests the possibility that a change in cell characteristics in the epithelial mesenchymal transition (EMT) occurs because the resistant cell line is modified into a migratory phenotype as compared to the parental cell line. In addition, the expression of vimentin, which is an EMT-related protein, was strongly increased in the cell lines resistant to an ALK inhibitor as compared to the parental cells. Furthermore, the increased expression of vimentin was clearly decreased by treatment with verteporfin and when YAP was deleted. Through the results, it can be seen that YAP also plays an important role in the proliferation of cancer cells and the metastasis of cancer in the cell line resistant to an ALK inhibitor.

Preparation Example 3. Construction of Model Acquiring Resistance to Crizotinib in Patient-Derived Tumor Xenograft (PDTX) Using Tissues from Patient with EML4-ALK Positive Non-Small Cell Lung Cancer A model that acquired resistance in vivo was constructed by continuously administering an ALK inhibitor to ALK-PDTX by a method similar to that in Preparation Example 1. In order to construct a model acquiring resistance to crizotinib from the constructed ALK-PDTX, the ALK-PDTX tissues were engrafted in a mouse, and then the group was separated when the tumor size became about 200 mm³. At the start, crizotinib at 25 mg/Kg (oral, daily) was administered to the separated group, the dose of crizotinib was gradually increased to 50 mg/Kg, 75 mg/Kg, 100 mg/Kg, and 150 mg/Kg whenever a 25% re-growth occurred from the maximum tumor reduction, so that the mouse was sacrificed when the tumor was not finally reduced even at a high concentration of 150 mg/Kg, and then a tissue of a tumor that had acquired resistance to crizotinib was secured. Moreover, a paraffin fragment was prepared from the tissue, and the expression of YAP was identified by an immunostaining method and is illustrated in FIG. 14. FIG. 14A illustrates a process of constructing a tumor tissue acquiring resistance to crizotinib by identifying the change in tumor size while crizotinib is administered to an ALK-PDTX tissue by gradually increasing the dose of crizotinib, and FIG. 14B illustrates a result of identifying the expression of YAP in the constructed tumor tissue that has acquired resistance to crizotinib through an immunostaining method.

As illustrated in FIG. 14, it was confirmed that the expression of YAP in the resistant tissue group was strongly increased as compared to that in the group which was not treated with crizotinib, and the inside of the nucleus was mainly stained. In addition, the expression of YAP was identified from a biopsy (biological tissue) before and after a patient with EML4-ALK positive non-small cell lung cancer was treated with crizotinib, and as a result, it was confirmed that the expression of YAP in a tissue where cancer again proceeded was increased after the treatment as compared to that before the treatment. Through the results, it can be seen that the activity of YAP in the nucleus is an important factor in acquiring resistance to an ALK inhibitor in the same manner as in the results in vitro.

The present invention relates to a novel medicinal use of a statin-based drug for treatment of EML4-ALK positive non-small cell lung cancer that has acquired resistance to an ALK inhibitor occurring when EML4-ALK positive non-small cell lung cancer is treated in the related art, and can provide a pharmaceutical composition exhibiting therapeutic efficacy against EML4-ALK positive non-small cell lung cancer that has acquired resistance to the ALK inhibitor. Further, the present invention can provide information for selecting a drug for treatment of EML4-ALK positive non-small cell lung cancer that has acquired resistance to an ALK inhibitor.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method comprising:
   confirming whether a resistance to an anaplastic lymphoma kinase (ALK) inhibitor has been acquired in a patient with EML4-ALK positive non-small cell lung cancer,
   confirming whether Yes-associated protein (YAP) is activated in the patient,
   selecting a statin-based drug for treatment of EML4-ALK positive non-small cell lung cancer when resistance to the ALK inhibitor has been acquired and YAP is activated in the patient, and
   administering to the patient who has acquired resistance to the ALK inhibitor and has activated YAP a pharmaceutical composition comprising a statin-based drug.

2. The method of claim 1, wherein the resistance to the ALK inhibitor is resistance to one or more ALK inhibitors selected from a group consisting of crizotinib, ceritinib, alectinib, brigatinib, and entrectinib.

3. The method of claim 1, wherein the statin-based drug is one or more selected from a group consisting of cerivastatin, rosuvastatin, simvastatin, atorvastatin, and fluvastatin.

4. The method of claim 3, wherein the statin-based drug is cerivastatin.

5. The method of claim 1, wherein the resistance to the ALK inhibitor is confirmed using an analysis method of an MTT assay or a colony formation assay.

6. The method of claim 1, wherein the activated YAP in the patient is confirmed by an increased expression of YAP.

\* \* \* \* \*